US011951297B2

(12) United States Patent
Kirchhoff et al.

(10) Patent No.: US 11,951,297 B2
(45) Date of Patent: Apr. 9, 2024

(54) METHOD OF MANUFACTURING A BLOOD PUMP

(71) Applicant: Abiomed Europe Gmbh, Aachen (DE)

(72) Inventors: Frank Kirchhoff, Aachen (DE); Josef Penners, Aachen (DE); Thorsten Siess, Aachen (DE); Werner Carell, Aachen (DE); Wolfgang Kerkhoffs, Aachen (DE)

(73) Assignee: Abiomed Europe Gmbh, Aachen (DE)

( * ) Notice: Subject to any disclaimer, the term of this patent is extended or adjusted under 35 U.S.C. 154(b) by 559 days.

(21) Appl. No.: 16/981,061

(22) PCT Filed: Mar. 22, 2019

(86) PCT No.: PCT/EP2019/057272
§ 371 (c)(1),
(2) Date: Sep. 15, 2020

(87) PCT Pub. No.: WO2019/180221
PCT Pub. Date: Sep. 26, 2019

(65) Prior Publication Data
US 2021/0001027 A1     Jan. 7, 2021

(30) Foreign Application Priority Data

Mar. 23, 2018 (EP) ..................... 18163758
Mar. 23, 2018 (EP) ..................... 18163761

(51) Int. Cl.
*A61M 60/122* (2021.01)
*A61M 60/13* (2021.01)
(Continued)

(52) U.S. Cl.
CPC .......... *A61M 60/416* (2021.01); *A61M 60/13* (2021.01); *A61M 60/174* (2021.01);
(Continued)

(58) Field of Classification Search
CPC . A61M 60/148; A61M 60/422; A61M 60/237
See application file for complete search history.

(56) References Cited

U.S. PATENT DOCUMENTS 5,921,913 A     7/1999   Siess
5,964,694 A * 10/1999   Siess ..................... H02K 15/14
                                                                            623/3.1
(Continued)

FOREIGN PATENT DOCUMENTS

CN         103095020 A     5/2013
EP          0764448 A2     3/1997
(Continued)

OTHER PUBLICATIONS

European Search Report for corresponding EP Application No. 18163761.2 dated Aug. 18, 2020 (8 pages).
(Continued)

*Primary Examiner* — Michael J D'Abreu
(74) *Attorney, Agent, or Firm* — Botos Churchill IP Law LLP (57) ABSTRACT

An intravascular blood pump comprises a pumping device including an impeller and an electric motor for driving the impeller. A rotor of the electric motor is rotatable about an axis of rotation and coupled to the impeller so as to be able to cause rotation of the impeller. An outer sleeve forms a casing of the pumping device, wherein stator components are fixed inside the outer sleeve by means of a casting compound. In a method of manufacturing the blood pump the stator components are placed on a molding base, including the outer sleeve to thereby form an interspace between the molding base and the outer sleeve in which the stator components are disposed. The casting compound is then injected into the interspace via the molding base to fix the stator components inside the outer sleeve. The outer sleeve
(Continued)

preferably comprises a magnetically conductive material to form a yoke of the electric motor.

30 Claims, 7 Drawing Sheets

(51) Int. Cl.
    *A61M 60/174*      (2021.01)
    *A61M 60/216*      (2021.01)
    *A61M 60/416*      (2021.01)
    *A61M 60/825*      (2021.01)
    *A61M 60/857*      (2021.01)

(52) U.S. Cl.
    CPC ........ *A61M 60/216* (2021.01); *A61M 60/825* (2021.01); *A61M 60/857* (2021.01); *A61M 2205/0211* (2013.01); *A61M 2205/273* (2013.01); *A61M 2207/00* (2013.01)

(56) References Cited

U.S. PATENT DOCUMENTS

| | | | |
|---|---|---|---|
| 6,158,984 A | 12/2000 | Cao et al. | |
| 7,011,620 B1 | 3/2006 | Siess | |
| 2005/0008509 A1* | 1/2005 | Chang | F04C 15/008 |
| | | | 417/410.3 |
| 2005/0196293 A1* | 9/2005 | Ayre | A61M 60/232 |
| | | | 417/353 |
| 2010/0041939 A1 | 2/2010 | Siess | |
| 2010/0121438 A1 | 5/2010 | Jarvik | |
| 2010/0261140 A1 | 10/2010 | Klee et al. | |
| 2015/0051436 A1* | 2/2015 | Spanier | A61M 60/122 |
| | | | 600/16 |
| 2016/0175503 A1 | 6/2016 | Smith et al. | |
| 2016/0256620 A1* | 9/2016 | Scheckel | A61L 29/02 |

FOREIGN PATENT DOCUMENTS

| | | |
|---|---|---|
| ES | 2202405 T3 | 4/2004 |
| WO | 9844619 A1 | 10/1998 |

OTHER PUBLICATIONS

International Search Report for International Application No. PCT/EP2019/057272 dated Jul. 2, 2019 (3 pages).
European Search Report for corresponding EP Application No. 18163758. 8 dated Sep. 25, 2018 (6 pages).
Written Opinion from corresponding Singapore Patent Application No. 11202007916X dated Apr. 1, 2022, (5 pp.).
Office Action issued in corresponding Indian Patent Application 202037045199 dated Aug. 4, 2022, 5 pages.
Office Action issued in corresponding Chinese Patent Application No. 201980020793.4 dated Apr. 19, 2023 (21 pp.).
Office Action issued in Israeli Patent Application No. 276567 dated Nov. 2, 2023 (5 pp.).
Office Action issued in Canadian Patent Application No. 3,094,838 dated Nov. 1, 2023 (6 pp.).

\* cited by examiner

METHOD OF MANUFACTURING A BLOOD PUMP

CROSS-REFERENCE TO RELATED APPLICATIONS

The present application is a national phase entry under 35 U.S.C. § 371 of International Application No. PCT/EP2019/057272, filed Mar. 22, 2019, published in English as International Publication No. WO 2019/180221 A1, which claims priority from European Patent Application Nos. 18163758.8 and 18163761.2, each filed Mar. 23, 2018, all of which are incorporated herein by reference.

FIELD OF THE INVENTION

This invention relates to an intravascular blood pump for percutaneous insertion into a patient's blood vessel, in particular to be advanced into the patient's heart, and in particular a method of manufacturing the intravascular blood pump.

BACKGROUND OF THE INVENTION

An intravascular blood pump designed to be inserted percutaneously into a patient's blood vessel, such as a femoral or axillary artery or vein, may be advanced into the patient's heart to act as a left ventricular assist device or right ventricular assist device. The blood pump may, thus, be referred to also as an intracardiac blood pump. An intravascular blood pump typically comprises a catheter and a pumping device attached to a distal end of the catheter. The catheter may contain supply lines, such as an electric line and a purge line. Throughout this disclosure, the term "distal" will refer to directions away from a user and towards the heart, whereas the term "proximal" will refer to directions towards a user.

The pumping device may comprise an electric motor and an impeller coupled to a rotor of the electric motor for rotation of the impeller about an axis of rotation. During operation of the blood pump, the impeller conveys blood from a blood flow inlet to a blood flow outlet of the blood pump, for instance through a flow cannula. The pump rate depends on the size of the pumping device. In particular, the efficiency of the electric motor included in the pumping device is highly dependent on the limited space. However, it is desirable to reduce the size of the pumping device, in particular its diameter, because of anatomical limitations for insertion into a blood vessel.

While the flow cannula and the catheter usually are sufficiently flexible for following the anatomical path of the blood vessel, the pumping device is rigid. Thus, in order to facilitate navigation of the blood pump through the patient's blood vessel into the patient's heart, it would be desirable to reduce not only the diameter but also the length of the rigid pumping device. Furthermore, a relatively long pumping device causes relatively strong kinks at the interface between the pumping device and the flow cannula and the catheter, respectively, during advancing the blood pump through a curved blood vessel, which may lead to kinks or breaking.

In known intravascular blood pumps having a micro motor for driving the impeller of the blood pump, e.g. the blood pump disclosed in WO 98/44619 A1, the stator or at least stator parts of the electric motor are encapsulated in a casting compound, such as a polymer material, e.g. epoxy. According to a method of manufacturing the micro motor disclosed in WO 98/44619 A1, the stator parts of the motor are placed on a mandrel, which is then inserted into a mold cavity. A casting compound is injected into the mold cavity to encapsulate the stator parts and to form a housing of the pumping device.

The described injection-molding process may be carried out in a vacuum atmosphere, which requires long production cycles, during which the respective mold is occupied until the casting compound is cured, which typically takes from about one hour to about 24 hours. Thus, a large number of molds has to be provided for being able to increase the number of produced pieces. However, the molds are expensive and have to be cleaned after each cycle. Furthermore, a release agent, such as a silicone, is usually necessary, which has to be removed from the finished products. The resulting electric motor has a relatively thick plastic housing, which serves as a corrosion protection as desired but does not add further value to the function of the blood pump. To the contrary, the plastic housing increases the diameter of the pumping device and is heat insulating, which may lead to undesired heating of the electric motor during operation of the blood pump.

SUMMARY OF THE INVENTION

It is therefore an object of the present invention to provide an intravascular blood pump having small outer dimensions while at the same time having an efficient electric motor for providing an increased pump rate, as well as a fast and cost-effective method of manufacturing such intravascular blood pump.

This object is achieved according to the present invention by a method of manufacturing an intravascular blood pump and a respective intravascular blood pump having the features of the independent claims. Preferred embodiments and further developments of the invention are specified in the claims dependent thereon.

According to an aspect of the invention, a method of manufacturing an intravascular blood pump is provided. In particular, an intravascular blood pump as outlined above is to be manufactured, which comprises a pumping device including an impeller and an electric motor for driving the impeller. The electric motor includes a stator and a rotor, wherein the rotor is rotatable about an axis of rotation and coupled to the impeller so as to be able to cause rotation of the impeller. For manufacturing the intravascular blood pump, a molding base, which is sized and shaped for receiving stator components thereon, is provided. The stator components, such as a coil winding and possibly other stationary components, are placed on the molding base. An outer sleeve, which may be considered as the outermost of the stator components, is then placed on the molding base, and thereby over the other stator components already placed on the molding base, to thereby form at least a portion of an outer surface of the blood pump and to form an interspace between the molding base and the outer sleeve in which the stator components are disposed. A casting compound, such as a polymer material, in particular a resin like epoxy, is then injected into said interspace via the molding base to fix the stator components inside, i.e. radially inwards relative to the outer sleeve.

By the manufacturing method according to the present invention an intravascular blood pump can be made which has an outer sleeve forming at least a portion of an outer surface of the pumping device, wherein stator components, like the coil winding, are fixed inside the outer sleeve by means of a casting compound. The stator components are fixed by the casting compound, i.e. they are secured against relative movement to each other, in particular also relative to the outer sleeve. Stator components which are fully surrounded by the casting compound, such as the coil winding, are encapsulated by the casting compound and the electrically active components are well insulated on both sides against blood and purge fluids to avoid any leakage current or electro corrosion.

According to the method, the outer sleeve may be regarded to form a housing of the pumping device (also denoted as pump casing below) by forming at least a portion of the outer surface of the pumping device. The housing, more specifically the outer sleeve, defines an outer surface of the blood pump, more specifically the pumping device, at least in an area in which the blood pump has a maximum outer diameter. Thus, in contrast to known intravascular blood pumps, the outer surface or housing is not formed by the casting compound but by the outer sleeve. The casting compound is completely disposed within the boundaries defined by the inner diameter of the outer sleeve. The outer sleeve provides a fluid tight barrier against blood or other fluids to protect the stator components from corrosion. The outer sleeve may also serve as a soft iron magnet yoke as will be described below.

In other words, the mold for injecting the casting compound is formed by the outer sleeve, i.e. the pump casing itself forms the mold or, more specifically, a first casing section of the pump casing is formed by the mold. The first casing section will be connected with a second casing section at a later time to complete the pump casing and, in particular, to complete a housing for the motor. Thus, the method of manufacturing according to the present invention does not need expensive molds, which are occupied during curing the casting compound. The casting compound is directly injected into the inside of the pumping device, more specifically into the interspace formed between the outer sleeve and the molding base. No cleaning of the finished product is required since the casting compound is only in the inside of the outer sleeve, unlike in known injection molding processes where typical casting compounds like epoxy may stick to undesired areas on the outer surface of the product and require removal of excess casting compound. This may be particularly relevant if delicate structures on the outer surface of the pumping device shall be free of casting compound, such as a groove for a sensor or the like. Furthermore, since the product does not have to be removed from a mold cavity, the method does not require any release agents, and there is no need for removing a release agent from the surface of the finished product. Being able to work without any release agent also reduces the risk of any undesirable contamination, which could lead to a long term break down of the desired insulation of the casting compound. At the same time, other components of the blood pump, in particular stationary components, including stationary components which are not necessarily part of the electric motor but which are located also inside the outer sleeve, can be easily fixed by the casting compound, e.g. the end of a purge line.

In contrast to known molds for an injection molding process, the molding base used in the method according to the present invention may be an easy to manufacture and cheap piece and can be produced e.g. by injection molding or other techniques, like rapid prototyping, lathing, or the like. The molding base can be formed as a disposable piece so that there is no need to wait for the casting compound to cure before another pumping device can be produced. The molding base, in particular if produced by injection-molding, may comprise a plastic material like polyethylene (PE), polypropylene (PP), polytetrafluoroethylene (PTFE), or other plastic materials suitable to withstand the injection molding process. PTFE allows for particularly easy removal of the molding base from the product after curing.

Forming the outer surface of the pumping device by the outer sleeve rather than by a casting compound has the further advantage that the outer diameter of the pumping device can be reduced because there is no additional casting compound that surrounds the pumping device to form a pump casing. For instance, the pump casing may have an outer dimension of 18 F (French) or smaller (i.e. an outer diameter of 6 mm or smaller). Despite the small dimensions, a pump rate of up to 5.5 liters per minute may be achieved. By reducing the amount of plastic material, heat transfer away from the pumping device may be improved because of the reduced plastic insulation. Furthermore, this may reduce the likelihood of breakage of the blood pump, in particular at interfaces between the pumping device and a catheter and a flow cannula, respectively, because stress peaks at these interfaces may be reduced.

The aforementioned advantages and effects become particularly effective if the outer sleeve comprises a magnetically conductive material to form a yoke (back iron) of the electric motor. Thus, the outer sleeve does not only form a casing without a further function but serves as the yoke for closing the magnetic flux of the electric motor. In particular, the outer sleeve may comprise or may be made of a metal or metal alloy, such as a ferritic alloy, e.g. a FeCrAl alloy. The outer surface of the sleeve may be covered with a respective oxide. It will be appreciated that the outer sleeve may comprise any suitable biocompatible magnetically conductive material. A metal material has the further advantage that heat dissipation is increased compared to a plastic material and may provide increased structural stability.

According to a particularly preferred embodiment, the first stator part to be placed on the molding base may be an inner sleeve such that the interspace for injecting the casting compound is formed between the inner sleeve and the outer sleeve. The inner sleeve then forms a cavity for receiving the rotor of the electric motor. In a preferred embodiment, the inner sleeve is made of a ceramic material, such as zirconia, or more preferably alumina toughened zirconia (ATZ). After placing the inner sleeve on the molding base, other stator parts may be placed on the molding base, more specifically on the inner sleeve, e.g. a coil winding, a bearing, a printed circuit board, an electric line, a purge line, etc.

By providing an inner sleeve made of a ceramic material a fluid tight enclosure of the cavity, in which the rotor is disposed, can be created. The ceramic material is diffusion resistant against the purge fluid. Thus, effective corrosion protection of the stator, in particular electric stator parts like the coil winding, can be achieved. Since in this preferred embodiment the ceramic sleeve rather than the inner surface of the casting compound forms the cavity for the rotor, corrosion protection does not depend on the precision of the injection molding process, but the ceramic material of the inner sleeve forms a secure barrier against the purge fluid.

Apart from the sealing properties of the ceramic material, the ceramic inner sleeve provides the advantage that it can be manufactured with very small manufacturing tolerances. Thus, e.g. by placing the coil winding on the ceramic sleeve before injection molding, the dimensions of the coil winding, in particular the inner diameter and, thus, the outer diameter, can be defined and adjusted very precisely. The ceramic sleeve is substantially rigid and good to handle and may improve handling of the coil winding once the coil winding is placed on the sleeve. For instance, the coil winding may be placed on the molding base together with the inner sleeve. The ceramic material allows for a very small wall thickness of the inner sleeve, which is important for not increasing the overall diameter of the pumping device and for maintaining a small air gap between the stationary coil and the rotating magnet in order to ensure a high motor efficiency and low core temperature.

The casting compound is preferably fed through the molding base and into said interspace between the molding base and the outer sleeve. That means, the molding base may be provided as a socket for the injection molding process and the molding base may have a port and one or more supply lines which are configured to supply the casting compound into the outer sleeve, more specifically into the interspace between the molding base and the outer sleeve or preferably into the interspace between the inner sleeve and the outer sleeve. In particular, the casting compound will not be supplied to the outside of the outer sleeve.

Injecting the casting compound may be carried out in a low-pressure atmosphere, in particular vacuum, in which the interspace is substantially evacuated. This may aid in drawing the casting compound into the interspace and distributing the casting compound all-over within the interspace and to fix or encapsulate the stator components in the interspace and to the outer sleeve.

In order to compensate for shrinking of the casting compound during a curing process, an excess amount of casting compound may be fed into and through the interspace into a reservoir. In other words, a riser may be provided to prevent bubbles or cavities due to shrinkage during curing of the casting compound. The reservoir is preferably placed outside the outer sleeve and connected to the interspace. This connection will be removed along with the reservoir after curing is completed. It will be appreciated that this is the only exception for casting compound to be fed to the outside of the outer sleeve. Nevertheless, in any case, the casting compound will not come into contact with the outer surface of the outer sleeve.

In one embodiment, the molding base may comprise a pin, preferably a metal pin, arranged along a central longitudinal axis of the molding base and protruding from the molding base. The pin may be sized and shaped to receive e.g. a purge line, which extends from the pumping device. The pin may form a portion of the molding base having the smallest diameter. Thus, a metal pin may improve stability of the molding base. The pin may be coated, e.g. with the plastic material used for the rest of the molding base. In other words, the pin may form a central core of the molding base.

Before the outer sleeve is placed on the molding base, an electric line may be connected, e.g. soldered, to at least one of the stator components, preferably the coil winding. The established electrical connection will then be fixed, in particular encapsulated, also by the casting compound. The electrical connection may be located on the ceramic inner sleeve described above.

Generally, the molding base in the method of manufacturing a blood pump according to the present invention may be denoted as molding inlay. The molding base may be formed as a mandrel. The mandrel is configured to receive the stator components and the outer sleeve thereon and may serve for centering all parts placed thereon. The molding base may have a substantially cylindrical body. More generally, the molding base has a convex body, in particular in contrast to concave molding cavities.

The molding base preferably has a shoulder, wherein a portion of the molding base with first outer diameter may correspond to a cavity for the rotor of the electric motor, and a portion of the molding base with second outer diameter, smaller than the first outer diameter, may correspond substantially to a central shaft of the rotor or a central aperture of a bearing, in particular a journal bearing.

In the above described method, the casting compound is cured after being injected into the interspace, wherein the molding base is preferably separated from a casting compound source before curing the casting compound. Thus, the molding base with the casting compound and the parts of the pumping device can be removed from an injection station and stored for curing. No mold is occupied, in particular if the molding base is a disposable piece. A plurality of molding bases may be placed on a support after the injection-molding process and stored for curing, while the injection process may be continued for further products. The method of the present invention is, thus, suitable for cost-effective mass production.

After the casting compound has been cured, the molding base is removed. No cleaning is required since the casting compound is disposed only in the interspace fixing the stator components and securing them in and to the outer sleeve. For improving precision of the injection-molding, the outer sleeve may be sealed against the molding base, e.g. by applying adhesive or glue at possible leakages before injecting the casting compound into the interspace, to prevent casting compound to leak out of the outer sleeve. Adhesive may also be applied at locations inside the outer sleeve to prevent casting compound to flow into certain stator compounds, such as a bearing.

The outer sleeve together with the stator components fixed therein form a first casing section. The cavity inside the outer sleeve in which the molding base is located during the manufacturing process will form a cavity for the rotor of the electric motor, in particular a magnet, which will be inserted into the cavity. Furthermore, a second casing section will be mounted against the first casing section so as to complete the housing for the motor, and an impeller may be coupled to a shaft connected to the rotor and extending out of the motor housing. Finally, a flow cannula forming a blood flow inlet and a blood flow outlet, a catheter, and other parts may be added to complete the intravascular blood pump.

In use, a purge fluid will be directed through the rotor cavity from proximal to distal and exit the motor housing where the rotor shaft extends out of the motor housing. In addition, purge fluid may seep through leaks, if any, at the interface between the first and second casing sections into the patient's blood. While this would not be critical, the purge fluid might further leak through micro cracks in the casting compound resulting from shrinkage of the casting compound during curing, and might reach the coil windings of the stator, which should be avoided. Therefore, according to a preferred embodiment, at least one sealing ring is provided between the outer sleeve and the inner sleeve of the stator components so as to form a seal there between and protect the coil winding contained in the interspace between the outer and inner sleeves accordingly against ingress of purge fluid.

If such sealing ring is provided prior to injecting and curing the molding compound in the interspace, molding compound may come in contact with the sealing ring and thereby negatively affect the sealing characteristics of the sealing ring. In this case, it is advantageous to provide a second sealing ring axially in row with the first sealing ring so that the second sealing ring protects the first sealing ring against the molding compound.

Since the first sealing ring may deteriorate over time due to its contact with the purge fluid, it is further preferred to dispose a sealing ring also between the first and second casing sections when mounting the second casing section against the first casing section so as to seal the first sealing ring against the rotor cavity and, thus, against the purge fluid.

Alternatively, instead of providing the afore-mentioned one or two or even three sealing rings, the first casing section may be mounted to the second casing section using a liquid sealing material between the first and second casing sections at an interface with the inner sleeve. The liquid sealing material completely fills all spaces and preferably wets and attaches to all surfaces in such spaces. Once the liquid sealing material is dry, the first casing section is sealingly connected to the second casing section at the interface with the inner sleeve, thereby preventing any purge fluid from reaching the casting compound surrounding the coil windings. Preferably, the dried liquid sealing material is elastic. For instance, an elastomeric material may be used as the liquid sealing material which—when cured and dry—provides elastic properties in order to provide proper sealing functions and also to compensate for shrinkage of the sealing material during curing.

BRIEF DESCRIPTION OF THE DRAWINGS

The foregoing summary, as well as the following detailed description of preferred embodiments, will be better understood when read in conjunction with the appended drawings. For the purpose of illustrating the present disclosure, reference is made to the drawings. The scope of the disclosure is not limited, however, to the specific embodiments disclosed in the drawings. In the drawings.

DETAILED DESCRIPTION

Figure 1:
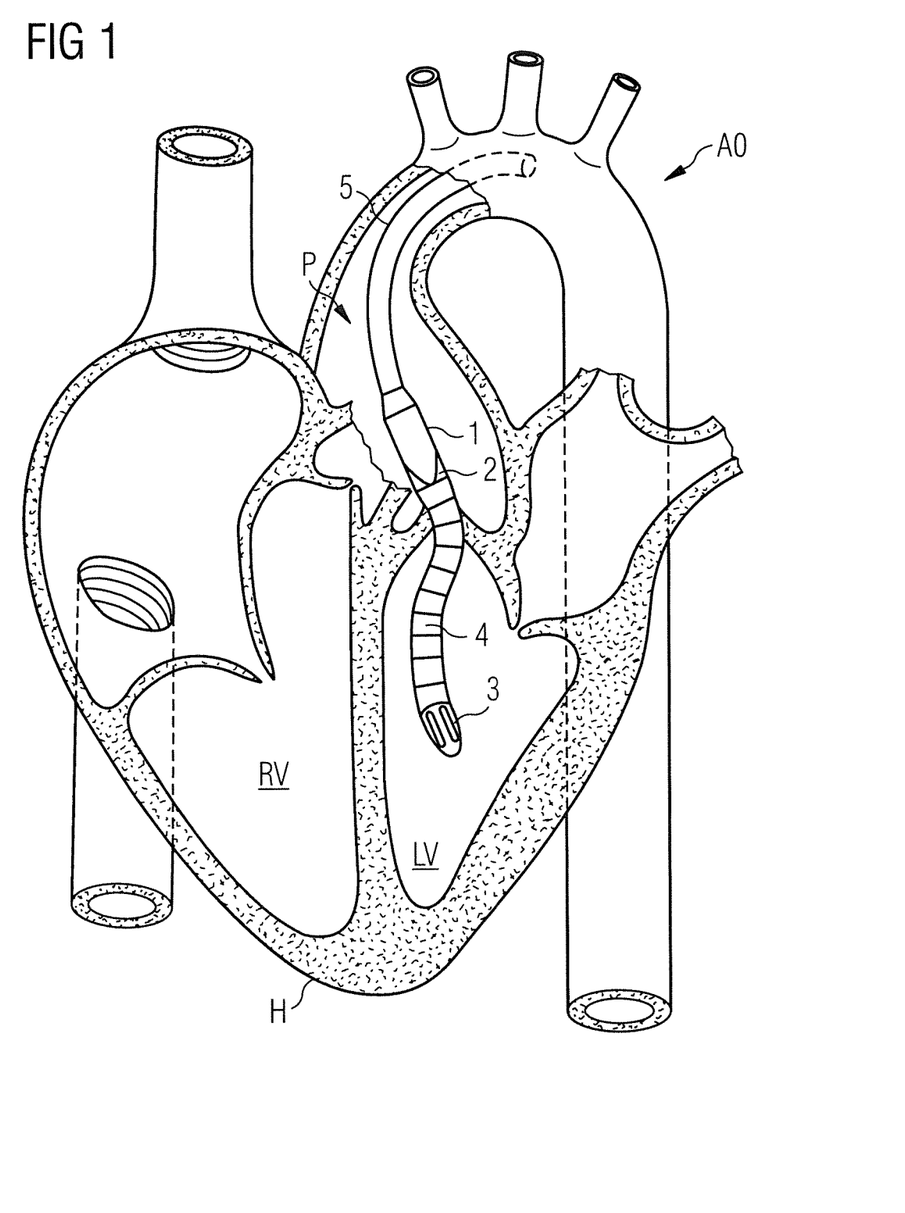
FIG. 1 schematically shows an intravascular blood pump inserted into a patient's heart.

In FIG. 1 is illustrated an intravascular blood pump P inserted into a patient's heart H. More specifically, the blood pump P comprises a pumping device 1 attached to a catheter 5 by means of which the pumping device 1 is inserted into the left ventricle LV of the patient's heart H to pump blood from the left ventricle LV into the aorta AO. The shown application is only an exemplary application, and the blood pump P of the present invention is not limited to this application. For instance, reverse applications for the right ventricle RV may be envisioned. The blood pump P is percutaneously inserted e.g. via a femoral access or an axillary access and is advanced through the aorta AO into the heart H. The blood pump P is placed such that a blood flow outlet 2 is disposed outside the patient's heart H in the aorta AO, while a blood flow inlet 3 which is in flow communication with a flow cannula 4 is disposed inside the left ventricle LV. An impeller is provided in the pumping device 1 to cause the blood flow from the blood flow inlet 3 to the blood flow outlet 2, and rotation of the impeller is caused by an electric motor disposed in the pumping device 1 as will be explained in more detail below.

Figure 2:
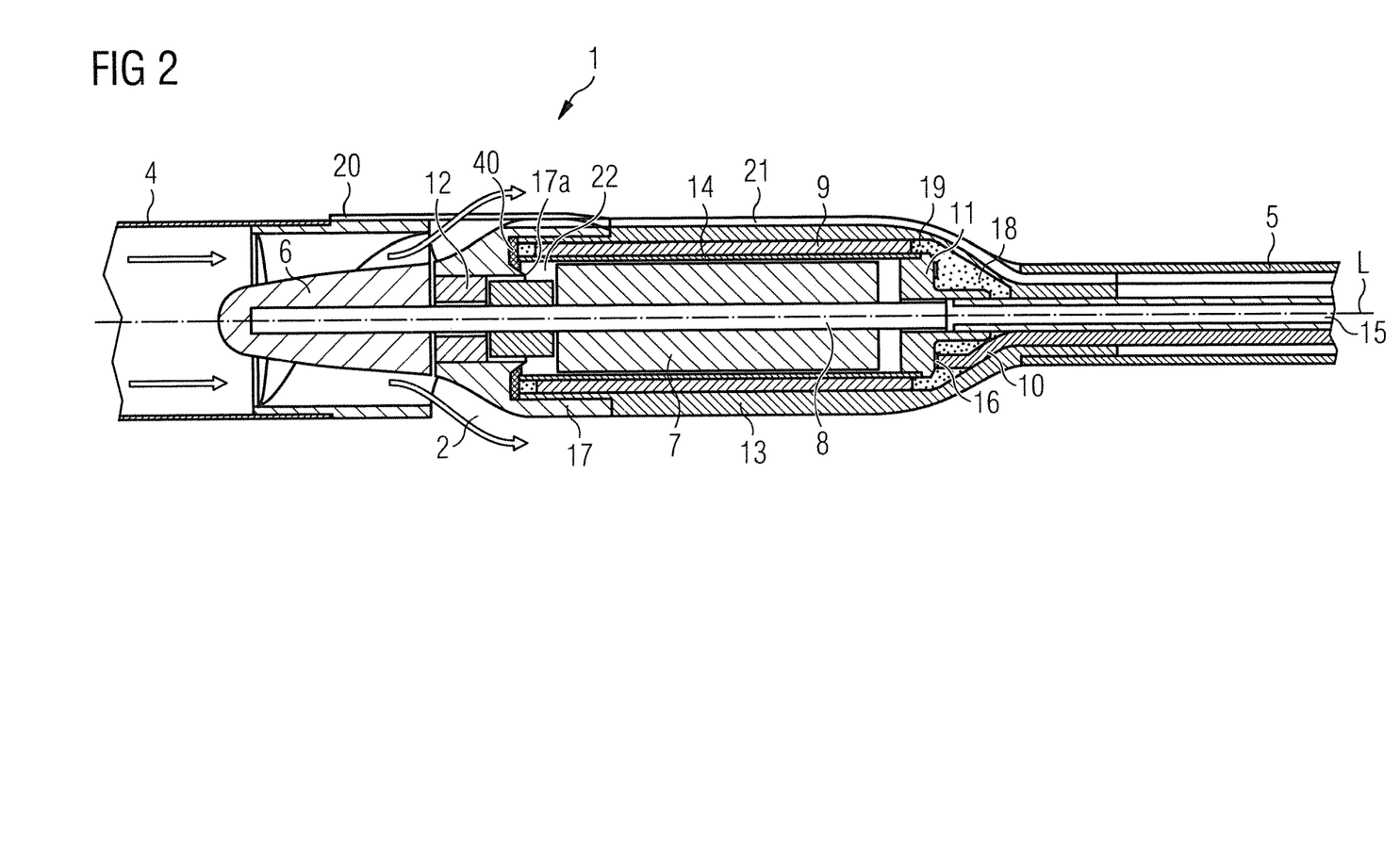
FIG. 2 shows a cross-section through an intravascular blood pump according to a first embodiment.

FIG. 2 shows a cross-sectional view through the pumping device 1 according to a first embodiment along a central longitudinal axis L, which is coincident with an axis of rotation of the rotor 7 and the impeller 6. More specifically, the rotor 7 and the impeller 6 are arranged on a common shaft 8 which extends along the axis of rotation. The rotor 7 of the electric motor is formed as a permanent magnet and is disposed inside a cavity 22 of the pump casing. In order to cause rotation of the rotor 7, a coil winding 9 as part of a stator of the electric motor surrounds the rotor 7 and is controllable so as to cause rotation of the rotor 7. The impeller 6 is coupled to the rotor 7 via the shaft 8 such that rotation of the rotor 7 causes rotation of the impeller 6 to thereby draw blood into the blood flow inlet 3 and through the flow cannula 4 out of the blood flow outlet 2 as indicated by the arrows in FIG. 2.

The shaft 8 is rotatably supported by a distal bearing 12 and a proximal bearing 11, both of which may be formed as a journal bearing as shown in FIG. 2. The bearings 11, 12 and the shaft 8 may be formed of a ceramic material. However, other types of bearings, such as ball bearings, may be used for rotatably supporting the shaft 8. The bearings may be axial bearings or radial bearings or combined axial and radial bearings. A purge fluid is supplied through the bearings 11, 12 and the cavity 22 in which the rotor 7 is located by means of a purge line 15. The purge line 15 extends through the catheter 5 and is connected to the proximal bearing 11 in a fluid tight manner. In this way, the purge fluid does not come into contact with electrical components of the pumping device 1 but only flows through the proximal bearing 11, into the cavity 22 and through the distal bearing 12.

In order to provide a secure barrier to protect the electrical components, in particular the coil winding 9, from corrosion and short circuits caused by the purge fluid, the cavity 22 for the rotor 7 may be formed by an inner sleeve 14, which is made of a ceramic material. The ceramic inner sleeve 14 is attached to the proximal bearing 11 in a fluid tight manner and is resistant against diffusion of the purge fluid. The ceramic inner sleeve 14 is so well defined also with a smooth inner surface that in another configuration of the blood pump some blood can be allowed to enter the pump instead of the purge fluid without clotting or blood destruction. Further corrosion protection is established by a casting compound 18, which fixes the stator components of the pumping device 1 and fills an interspace 19 between the inner sleeve 14 and an outer sleeve 13. In particular, the coil winding 9 is encapsulated in the casting compound 18. The casting compound 18 also provides additional fixation for the electrical connections 16 (i.e. a printed circuit board PCB) with the motor cable 10 as well as the purge line 15. The casting compound 18 may be a polymer material like a resin, preferably a two-component epoxy, and more preferably a two-component epoxy with a heat conducting and electrically insulating filler.

The outer sleeve 13 defines the outer surface and the outer dimensions of a part of the pumping device 1. Thus, a first section of the casing of the pumping device 1 is defined by the outer sleeve 13 enclosing the aforementioned components, in particular the stator components fixed by the casting compound 18. It will be appreciated that the outer sleeve 13 also forms a stator component, which is magnetically active. The outer sleeve 13 is made of a biocompatible magnetically conductive material, such as a suitable metal alloy, and serves as a yoke for the magnetic flux of the electric motor. The metal outer sleeve 13 also allows for good dissipation of heat caused by operation of the electric motor. The outer surface of the outer sleeve 13 may include a groove 21 for receiving a line with a sensor 20. A hub 17 is attached to the distal end of the outer sleeve 13 and forms an attachment area for the flow cannula 4. The hub 17 is preferably made of the same material as the outer sleeve 13 and accommodates the distal bearing 12 and the impeller 6. The blood flow outlet 2 is formed in the hub 17, such that heat transfer away from the distal bearing 12 is possible.

The outer sleeve 13 may have a length of about 7 mm to about 30 mm, preferably about 10 mm to about 20 mm, more preferably about 10 mm to about 15 mm. The outer sleeve 13 may have an outer dimension of 18 F (French) or smaller (outer diameter of 6 mm or smaller). Despite the small dimensions, a pump rate of up to 5.5 liters per minute may be achieved.

Figure 3A:
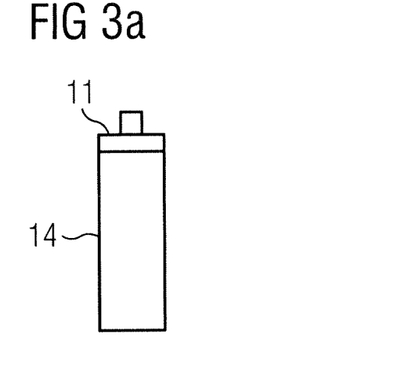
FIGS. 3a to 3f schematically show steps of a method of manufacturing a first casing section for the intravascular blood pump according to the first embodiment.

Now referring to FIGS. 3a to 3f, steps of a method of manufacturing the aforementioned first casing section of the intravascular blood pump as shown in FIG. 2 is described. First, as shown in FIG. 3a, the ceramic inner sleeve 14 may be provided and attached to the ceramic end piece 11 which includes the proximal bearing as explained above. Attaching the ceramic inner sleeve 14 to the ceramic end piece 11 may be realized e.g. by bonding or by means of one or preferably two or more preferably three consecutive sealing rings (not shown). That is, one sealing ring may be provided on the cavity-side of a main sealing ring in order to protect the main sealing ring from contact with purge fluid during use of the blood pump, whereas another sealing ring may be provided on the opposite side of the main sealing ring so as to protect the main sealing ring against casting compound which might enter through the interface between the ceramic inner sleeve 14 and the ceramic end piece 11 during the manufacturing process of the first casing section, as will be explained further below.

Figure 3B:
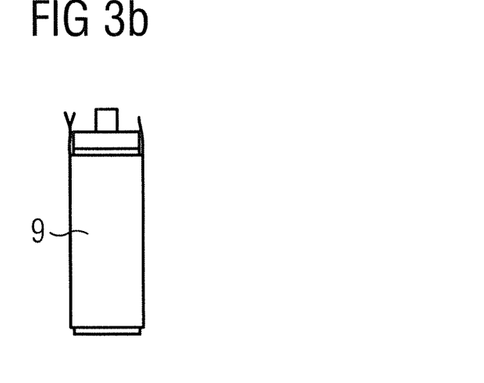
Figure 3C:
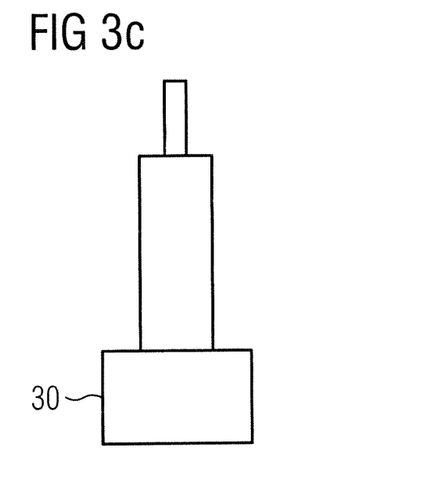
Figure 3D:
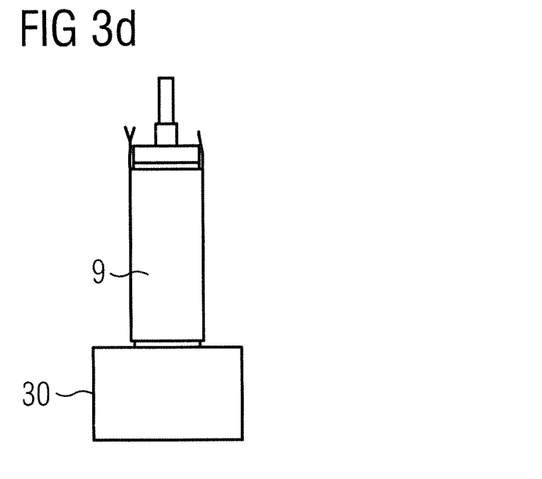
Figure 3E:
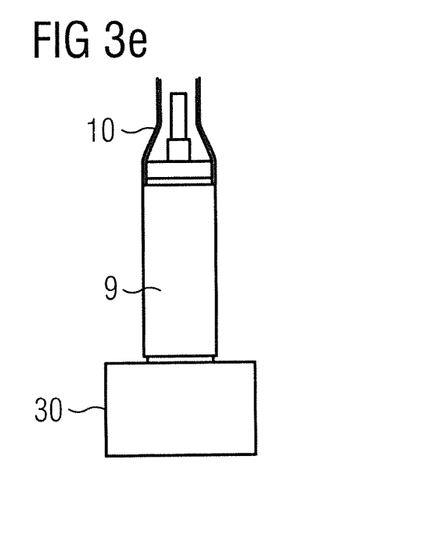
Figure 3F:
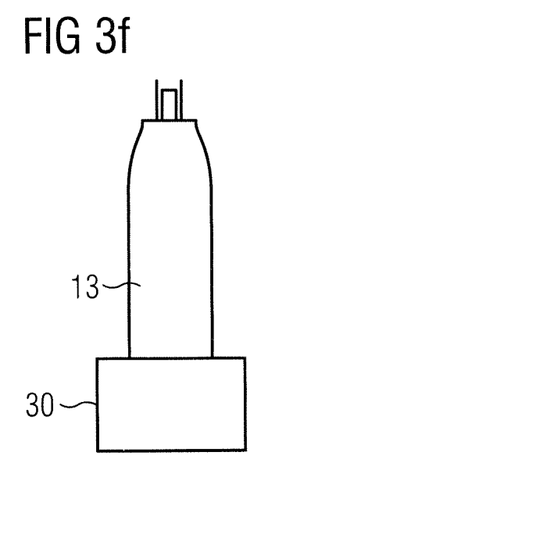

A pre-wound coil winding 9 is then placed on the sleeve 14 as shown in FIG. 3b. A molding base 30 is provided (FIG. 3c), which is formed as a mandrel sized and shaped for receiving the stator components of the pumping device 1. The coil winding 9 with the ceramic sleeve 14 is placed on the molding base 30 as shown in FIG. 3d. Alternatively, the coil winding 9 may be placed on the inner sleeve 14 after the inner sleeve 14 has been placed on the molding base 30. It will be appreciated that alternatively the inner sleeve 14 (i.e. the steps shown in FIGS. 3a and 3b) may be omitted, and the coil winding 9 may be placed directly on the molding base 30 without the inner sleeve 14. In order to protect the proximal bearing, i.e. to avoid that casting compound enters the bearing and contaminates the bearing surface, the proximal bearing may be sealed, as will explained further in connection with FIG. 4. The motor cable 10 is electrically connected to the coil winding 9, in particular soldered, as shown in FIG. 3e. Moreover, the purge line 15 is attached to the end piece 11 (not shown here).

Then, the outer sleeve 13 is placed over the molding base 30 to form an outer surface of the pumping device 1. Casting compound, such as epoxy, is then injected into the outer sleeve 13, more specifically into the interspace 19 formed between the inner sleeve 14 and the outer sleeve 13 containing the coil winding 9 to encapsulate the coil winding 9. In order to compensate for shrinkage during curing, a riser 19a (see FIG. 4) with a reservoir (not shown) may be provided for the casting compound. After finishing the injection-molding step, which may be carried out in a vacuum, the molding base 30 with the injected casting compound may be stored for curing.

In the meantime, further pumping devices may be produced in the same manner and stored for curing. No expensive molds are needed which are occupied during the curing process, which requires long production cycles. The molding base 30 is formed as a cheap disposable plastic piece and can be easily removed from the finished product. No release agent is needed. The casting compound does not come into contact with delicate parts of the pumping device. Thus, no cleaning of delicate surface structures, e.g. the aforementioned groove 21, is required.

Figure 4:
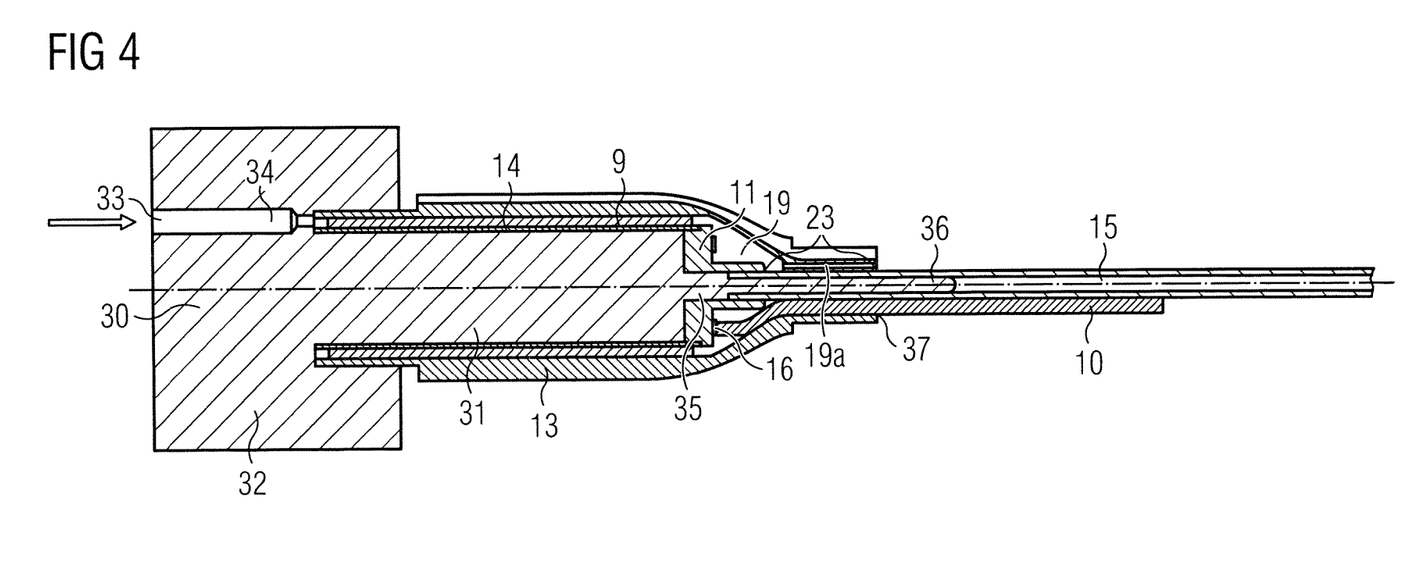
FIG. 4 shows a cross-section through the molding base used in the method of manufacturing the first casing section for the intravascular blood pump according to the first embodiment with stator components placed thereon.
Figure 5A:
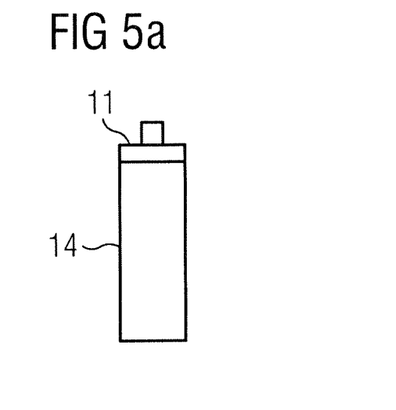
FIGS. 5a to 5f schematically show steps of a method of manufacturing a first casing section for the intravascular blood pump according to a second embodiment.
Figure 5B:
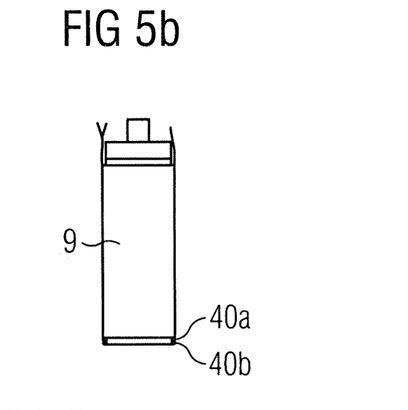
Figure 5C:
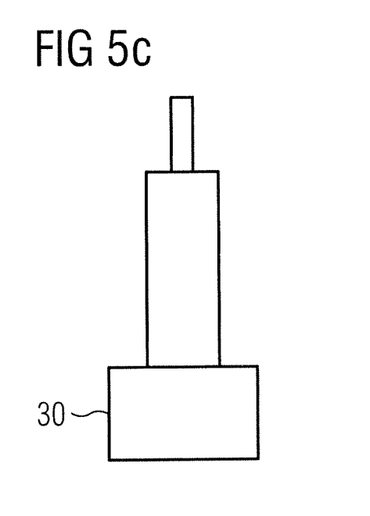
Figure 5D:
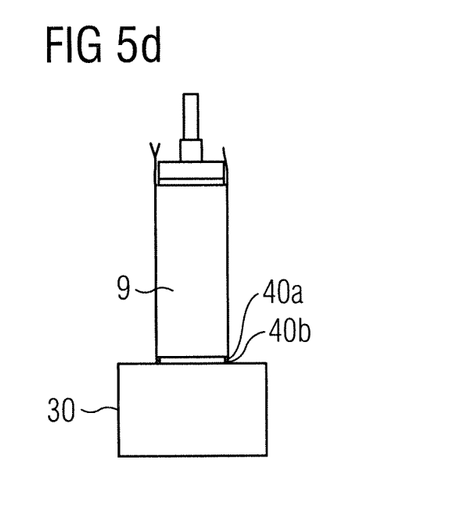
Figure 5E:
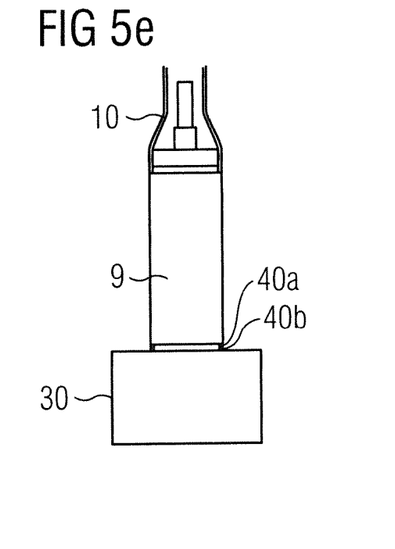
Figure 5F:
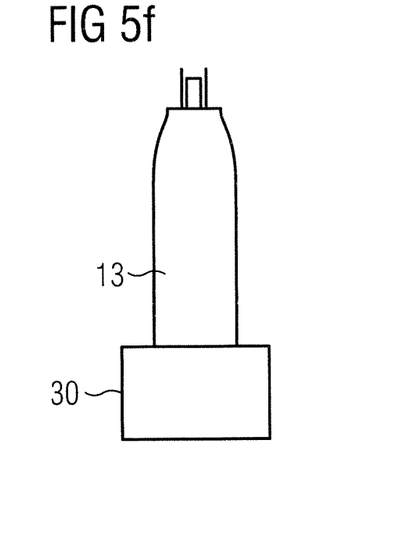

FIG. 4 shows a cross-section through the molding base 30 with all desired stator components, including the outer sleeve 13, placed thereon before injecting the casting compound 18. In particular, the ceramic inner sleeve 14 connected to the proximal bearing 11 and carrying the coil winding 9 is disposed on the molding base 30. However, it will be appreciated that the inner sleeve 14 may be omitted, and the coil winding 9 may be placed directly on the molding base 30. The motor cable 10 has been connected, in particular soldered, to the electrical connections 16 of the coil winding 9, i.e. the PCB. The purge line 15 is secured to the end piece 11 so as to be in fluid communication with the cavity 22 for the rotor 7 (see FIG. 2). The metal outer sleeve 13 covers all components and encloses the interspace 19 into which the casting compound will be injected. An interior surface of a proximal end of the end piece 11 and an external surface of a distal end of the purge line 15 may be sealed against each other by an adhesive 23 to prevent leakage of the casting compound 18 from the interspace 19 into the outer sleeve during the injection process. As can be seen in FIG. 2, the purge line 15 and the motor cable 10 extend through a proximal end of the outer sleeve 13, which will be attached to a distal end of the catheter 5. Accordingly, an interior surface of a proximal end of the outer sleeve 13 and external surfaces of the purge line 15 and motor cable 10 may be sealed against each other by an adhesive 23 to prevent leakage of the casting compound 18 from the interspace 19 to the surroundings during the injection process.

The molding base 30 is produced as an injection-molded disposable plastic piece and has a substantially cylindrical body portion 31 to form a mandrel. In particular, the body portion 31 is sized and shaped to receive the ceramic inner sleeve 14 thereon, or in other words to correspond to the cavity 22 for receiving the rotor 7 in the finished product. A socket portion 32 includes an injection port 33 and a supply line 34 for feeding the casting compound 18 into the interspace 19 between the inner sleeve 14 and the outer sleeve 13. At an end of the molding base 30 opposite the socket portion 32, a reduced diameter portion 35 extends from the main body portion 32 to receive the bearing 11. Further, a pin portion 36 extends from the portion 35 to receive the purge line 15 thereon. Although shown as an integral portion, the pin portion 36 may be formed as a metal pin for increased stability. The molding base 30 may be made e.g. of polytetrafluorethylene, polyethylene or polypropylene.

The casting compound 18 is injected into the injection port 33 as indicated by the arrow. An excess amount of casting compound 18 may be injected into and through the interspace 19 into a reservoir (not shown) via a riser 19a to compensate for shrinkage of the casting compound 18 during curing. The reservoir may be attached to the riser 19a at a proximal surface 37 of the outer sleeve 13. After the casting compound 18 has cured, the molding base 30 is removed, if applicable after removing the reservoir, and the first casing section is finished. No cleaning of the outer surface of the outer sleeve 13 is necessary because the casting compound 18 does not come into contact with the outer surface.

Thereafter, referring to FIG. 2 again, the rotor 7, i.e. the magnet, is mounted in the cavity 22 of the pump casing 1 along with the hub 17 and the distal bearing 12, and the impeller 6 is coupled to the rotor 7. The hub 17 constitutes a second casing section and forms together with the first casing section the housing for the rotor 7. In order to prevent that purge fluid can reach the cured casting compound and possibly migrate through micro cracks in the casting compound towards the coil winding 9 during use of the blood pump, a liquid sealing material 40 is provided between the first and second casing sections, more specifically between the inner sleeve 14 and the hub 17, and dried. In doing so, the hub 17 is placed vertically with its proximal end standing up, the liquid sealing material 40 is filled into an inner circumferential groove 17a of the hub 17 so as to fill the groove only partly, and the first casing section is placed onto the hub 17 such that a distal end of the inner sleeve 14 reaches into the liquid sealing material 40. The liquid sealing material is then cured to form the seal. Preferably, the liquid sealing material 40 is an elastomeric material so that the seal has elastic properties. Finally, the cannula 4 and the catheter 5 are attached to the pump casing 1. It will be appreciated that not all of the aforementioned method steps may be included in the method of the present invention, or other steps may be carried out if necessary as will be appreciated by a person skilled in the art. Likewise, the order of some of the described method steps may be changed if necessary.

Figure 6:
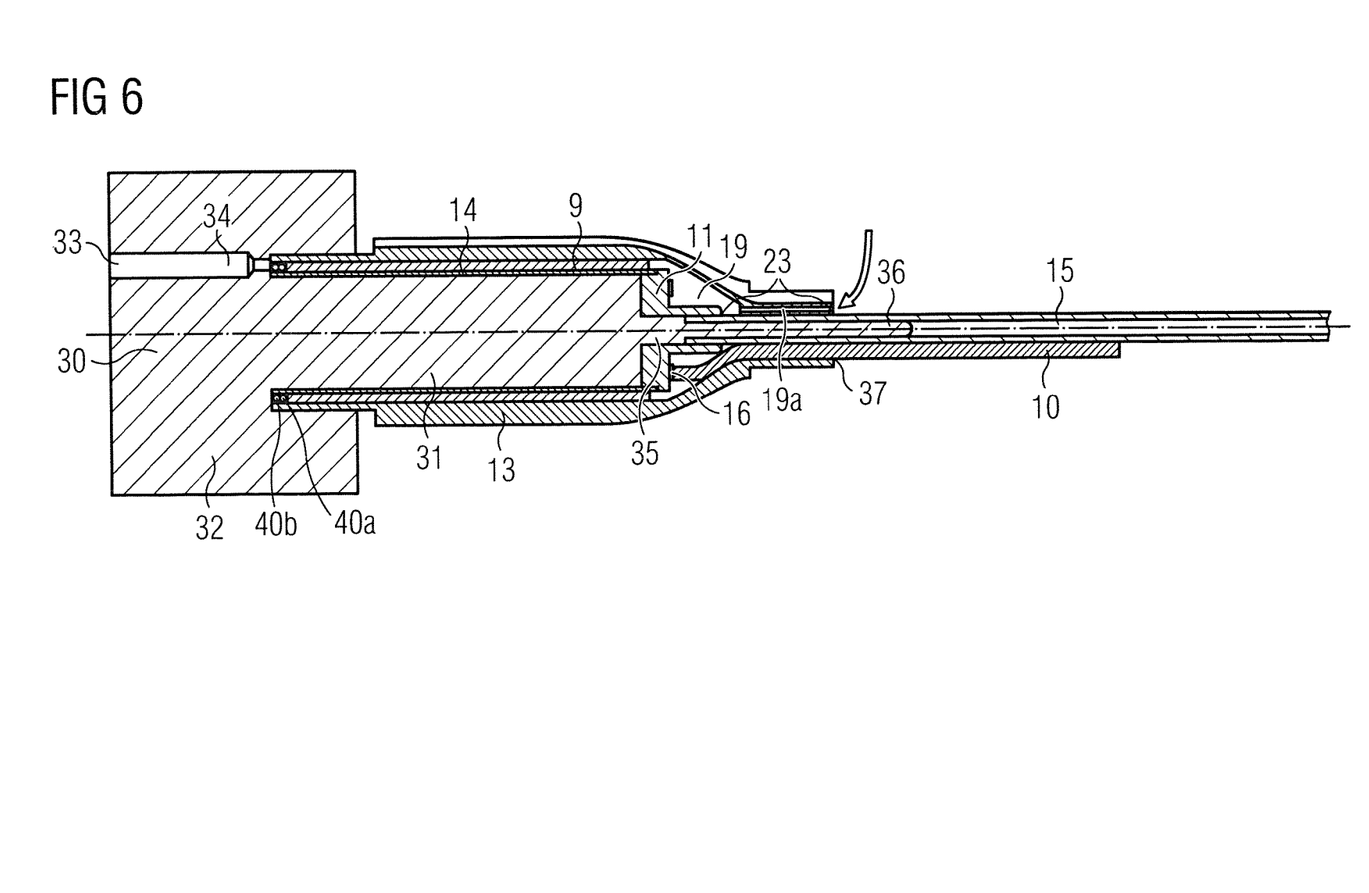
FIG. 6 shows a cross-section through the molding base used in the method of manufacturing the first casing section for the intravascular blood pump according to the second embodiment with stator components placed thereon.
Figure 7:
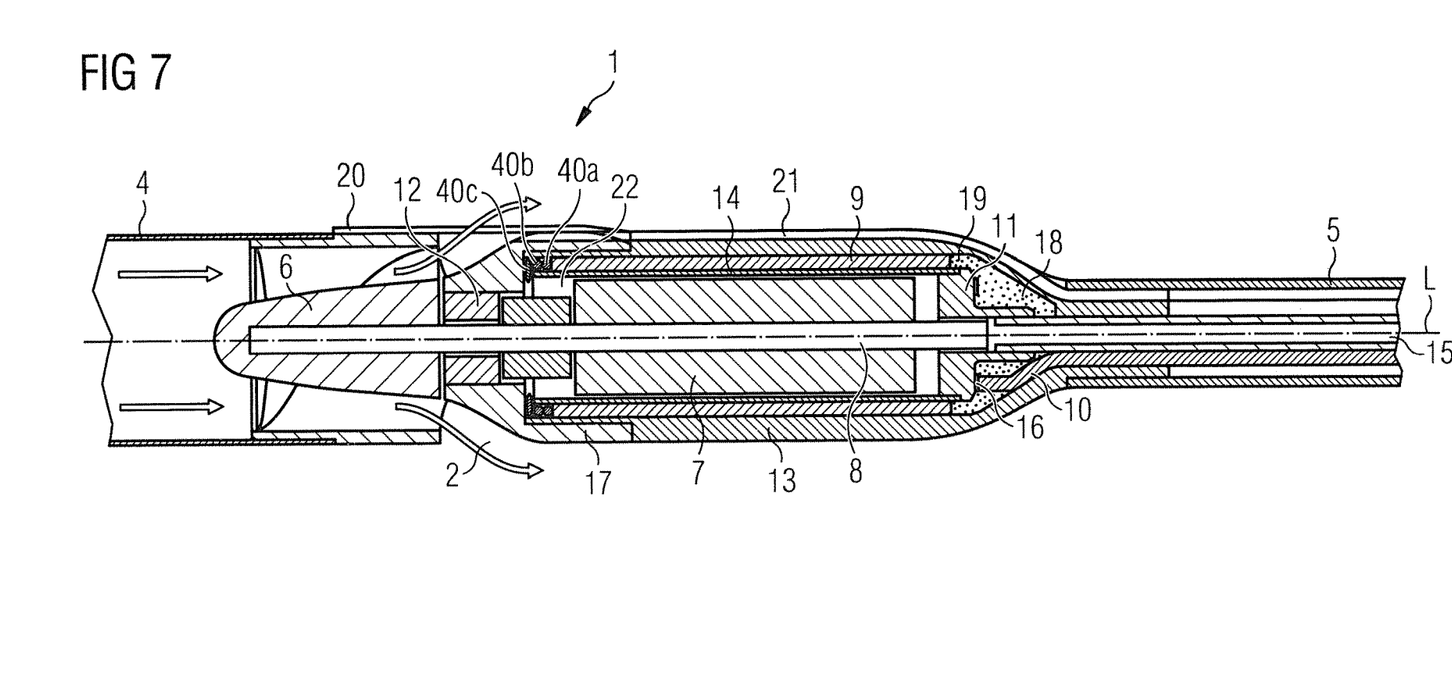
FIG. 7 shows a cross-section through an intravascular blood pump according to the second embodiment comprising the first casing section shown in FIG. 6.

FIGS. 5 to 7 relate to a second embodiment which differs from the first embodiment only in that the (dried) liquid sealing material 40 is omitted and a number of sealing rings 40a to 40c are used instead. Accordingly, FIGS. 5a to 5f, which schematically illustrate the steps of manufacturing the first casing section for the intravascular blood pump according to the second embodiment, differ from FIGS. 3a to 3f only in that in the step described in relation to FIG. 5b a first polymeric sealing ring 40a and a second polymeric sealing ring 40b are provided consecutively at the bottom or distal end of the coil winding 9. Thus, as can be seen in FIG. 6 showing a cross-section through the molding base 30 with all stator components placed thereon prior to injecting the casting compound 18 in the interspace 19, the two sealing rings 40a, 40b form a seal at the bottom of the molding base 30. In this second embodiment, the casting compound is supplied to the cavity 19 through the riser 19a, as indicated by the arrow, after the interspace 19 has been evacuated. Thus, the casting compound will reach the first sealing ring 40a, but not the second sealing ring 40b. Then, when the hub 17 is mounted to the first casing section, a third sealing ring 40c may be placed in the hub 17 such it contacts the inner sleeve 14 and thereby forms a seal between the hub 17 and the first casing section. This way, purge fluid flowing through the cavity 22 during use of the blood pump is prevented from reaching the second sealing ring 40b. Thus, the second sealing ring 40b is completely protected from both sides and can provide a proper sealing function over a long time.

The invention claimed is:

1. A method of manufacturing an intravascular blood pump, the blood pump comprising a pumping device including an impeller and an electric motor for driving the impeller, the electric motor including a stator and a rotor, the rotor rotatable about an axis of rotation and coupled to the impeller so as to be able to cause rotation of the impeller, the method comprising the steps of:
   providing a molding base sized and shaped for receiving stator components thereon;
   placing the stator components on the molding base by placing an inner sleeve on the molding base, the inner sleeve forming a cavity for receiving the rotor;
   placing an outer sleeve on the molding base to thereby form at least a portion of an outer surface of the blood pump and an interspace between the inner sleeve and the outer sleeve in which the stator components are disposed; and
   injecting a casting compound into the interspace via the molding base to fix the stator components inside the outer sleeve.

2. The method according to claim 1, wherein the step of placing the stator components on the molding base by placing the inner sleeve on the molding base includes forming the interspace for injecting the casting compound between the inner sleeve and the outer sleeve.

3. The method according to claim 2, comprising the step of providing at least one sealing ring between the outer sleeve and the inner sleeve so as to form a seal there between.

4. The method according to claim 3, wherein two of the at least one sealing ring are provided axially in a row.

5. The method according to claim 3, further comprising the steps of:
   curing the casting compound to form a first casing section, and
   mounting a second casing section against the first casing section with a further sealing ring disposed between the first and second casing sections so as to seal the at least one sealing ring against the cavity.

6. The method according to claim 2, further comprising the steps of:
   curing the casting compound to form a first casing section,
   mounting the first casing section to a second casing section with a liquid sealing material arranged between the first casing section and the second casing section at an interface with the inner sleeve, and
   curing the liquid sealing material to sealingly connect the first casing section to the second casing section at the interface with the inner sleeve.

7. The method according to claim 1, wherein the outer sleeve comprises a magnetically conductive material to form a yoke of the electric motor.

8. The method according to claim 7, wherein the outer sleeve comprises a metal or metal alloy.

9. The method according to claim 1, wherein the molding base is a disposable part.

10. The method according to claim 9, wherein the molding base is provided as an injection molded part.

11. The method according to claim 1, wherein the molding base comprises a polymer.

12. The blood pump according to claim 11, wherein the polymer is polyethylene, polypropylene or polytetrafluoroethylene.

13. The method according to claim 1, wherein the molding base comprises a pin arranged along a central longitudinal axis of the molding base and protruding from the molding base.

14. The method according to claim 13, wherein the pin is provided as a metal pin.

15. The method according to claim 1, wherein the casting compound comprises a polymer material.

16. The method according to claim 15, wherein the polymer material is an epoxy resin.

17. The method according to claim 1, wherein the step of injecting the casting compound includes feeding the casting compound through the molding base into the interspace.

18. The method according to claim 1, wherein the step of injecting the casting compound is carried out in a low-pressure atmosphere, in which the interspace is substantially evacuated.

19. The method according to claim 1, wherein the step of injecting the casting compound comprises feeding an excess amount of casting compound into and through the interspace into a riser.

20. The method according to claim 1, wherein the method further comprises the step of sealing the outer sleeve against the outside before the step of injecting the casting compound.

21. The method according to claim 1, further comprising the step of connecting an electric line to at least one of the stator components before the step of placing the outer sleeve on the molding base.

22. An intravascular blood pump for percutaneous insertion into a patient's blood vessel, comprising a pumping device including an impeller and an electric motor for driving the impeller, the electric motor including a stator and a rotor, the rotor rotatable about an axis of rotation and coupled to the impeller so as to be able to cause rotation of the impeller, the blood pump further comprising an inner sleeve configured to form a cavity for receiving the rotor and an outer sleeve configured to form at least a portion of an outer surface of the pumping device, wherein stator components are fixed inside the outer sleeve by means of a casting compound.

23. The intravascular blood pump according to claim 22, wherein the inner sleeve is arranged inside the outer sleeve to form an interspace between the inner sleeve and the outer sleeve in which the stator components are fixed by the casting compound are disposed.

24. The intravascular blood pump according to claim 23, comprising at least one sealing ring between the outer sleeve and the inner sleeve forming a seal there between.

25. The intravascular blood pump according to claim 24, wherein two of the at least one sealing ring are provided axially in a row.

26. The intravascular blood pump according to claim 24, comprising a further sealing ring disposed so as to seal the at least one sealing ring against the cavity.

27. The intravascular blood pump according to claim 23, wherein the inner sleeve is made of a ceramic material.

28. The intravascular blood pump according to claim 23, comprising a dried liquid sealing material disposed at an interface with the inner sleeve so as to seal the casting compound in the interspace against the cavity.

29. The intravascular blood pump according to claim 22, wherein the outer sleeve comprises a magnetically conductive material to form a yoke of the electric motor.

30. The intravascular blood pump according to claim 29, wherein the outer sleeve comprises a metal or metal alloy.

* * * * *

UNITED STATES PATENT AND TRADEMARK OFFICE
CERTIFICATE OF CORRECTION

| | |
|---|---|
| PATENT NO. | : 11,951,297 B2 |
| APPLICATION NO. | : 16/981061 |
| DATED | : April 9, 2024 |
| INVENTOR(S) | : Frank Kirchhoff et al. |

It is certified that error appears in the above-identified patent and that said Letters Patent is hereby corrected as shown below:

In the Specification

Column 10, Line 65:
Now reads: "32"; should read -- 31 --

Column 11, Line 61:
Now reads: "19"; should read -- 22 --

Signed and Sealed this
Twenty-fifth Day of June, 2024

Katherine Kelly Vidal
*Director of the United States Patent and Trademark Office*